(12) United States Patent
Kasurak et al.

(10) Patent No.: US 12,178,836 B2
(45) Date of Patent: Dec. 31, 2024

(54) KOMBUCHA NATURAL HEALTH PRODUCTS

(71) Applicant: VIVA NATURALS, INC., Toronto (CA)

(72) Inventors: Ashley Kasurak, Toronto (CA); Husayn Remtulla, Toronto (CA)

(73) Assignee: Viva Naturals, Inc., Toronto (CA)

( * ) Notice: Subject to any disclaimer, the term of this patent is extended or adjusted under 35 U.S.C. 154(b) by 0 days.

(21) Appl. No.: 18/352,356

(22) Filed: Jul. 14, 2023

(65) Prior Publication Data

US 2023/0355703 A1 Nov. 9, 2023

Related U.S. Application Data

(62) Division of application No. 17/828,129, filed on May 31, 2022, now Pat. No. 11,744,871.

(30) Foreign Application Priority Data

Jun. 14, 2021 (CA) ................................ CA 3122201

(51) Int. Cl.
*A61K 36/82* (2006.01)
*A23L 33/105* (2016.01)
*A23L 33/125* (2016.01)
*A23L 33/135* (2016.01)
*A23P 20/10* (2016.01)
*A61K 9/00* (2006.01)
*A61K 35/741* (2015.01)
*A61K 47/12* (2006.01)
*A61K 47/26* (2006.01)
*A61K 47/46* (2006.01)

(52) U.S. Cl.
CPC ............ *A61K 36/82* (2013.01); *A23L 33/105* (2016.08); *A23L 33/125* (2016.08); *A23L 33/135* (2016.08); *A23P 20/10* (2016.08); *A61K 9/0056* (2013.01); *A61K 35/741* (2013.01); *A61K 47/12* (2013.01); *A61K 47/26* (2013.01); *A61K 47/46* (2013.01); *A23V 2002/00* (2013.01)

(58) Field of Classification Search
CPC .... A61K 36/82; A61K 9/0056; A61K 35/741; A61K 47/12; A61K 47/26; A61K 47/46; A23L 33/105; A23L 33/125; A23L 33/135; A23P 20/10; A23V 2002/00
See application file for complete search history.

(56) References Cited

U.S. PATENT DOCUMENTS

2010/0291245 A1 11/2010 Gao et al.
2013/0309291 A1 11/2013 Stoll

FOREIGN PATENT DOCUMENTS

CN 1864508 A 11/2006
CN 102488122 6/2012
CN 107319447 11/2017

OTHER PUBLICATIONS

Aboulwafa et al., "A Comprehensive Insight on the Health Benefits and Phytoconstituents of Camellia sinensis and Recent Approaches for Its Quality Control", Antioxidants vol. 8, 455 Oct. 6, 2019, pp. 1 to 33.
Chaiyata et al., "Effect of chili pepper (*Capsicum frutescens*) ingestion on plasma glucose response and metabolic rate in Thai women" J Med Assoc Thai Sep. 2003; vol. 86(9), pp. 854-860.
Deal et al., "Treatment of arthritis with topical capsaicin: a double-blind trial" Clin There. May-Jun. 1991;vol. 13(3): pp. 383 to 395.
Delgado Montero R, Flores Cortez D, Villalobos Pacheco E. Efecto del Capsicum annum L (pucunucho, ají mono) en úlcera gástrica experimental inducida en ratas [Effect of *Capsicum annum* L (pucunucho, ají mono) in gastric ulcer experimentally induced in rats]. Rev Gastroenterol Peru. Apr.-Jun. 2015;35(2):141-6. PMID: 26228980.
Galgani et al., "Effect of dihydrocapsiate on resting metabolic rate in humans"; Am J Clin Nutr 2010; vol. 92: pp. 1089 to 1093.
Janessens et al., "Capsaicin increases sensation of fullness in energy balance, and decreases desire to eat after dinner in negative energy balance", Appetite, vol. 77, Jun. 2014, pp. 46 to 51.
Jayabalan et al., "A Review on Kombucha Tea—Microbiology, Composition, Fermentation, Beneficial Effects, Toxicity, and Tea Fungus", Comprehensive Reviews in Food Science and Food Safety vol. 13, 2014.
Ludy et al., "The effects of hedonically acceptable red pepper doses on thermogenesis and appetite" Physiol Behav. Mar. 1, 2011; vol. 102(3-4): pp. 251 to 258.

(Continued)

*Primary Examiner* — Robert A Wax
*Assistant Examiner* — Quanglong N Truong
(74) *Attorney, Agent, or Firm* — Sand, Sebolt & Wernow Co., LPA

(57) ABSTRACT

Kombucha tea faces many challenges concerning its use for its health benefits, such as standardization, as well as the determination of a specific dosage form appropriate to the intended use. Kombucha tea, as a fermented, alcohol-containing beverage that relies on a complex combination of living yeast and bacteria for production, is especially difficult to administer. The present invention provides a consistent, standardized dosage form and novel combinations of a traditional medicinal drink that is otherwise unsuitable for widespread natural medicine. By providing kombucha as a soft, chewable and orally dissolvable and/or disintegrable compositions, such as a gummie, a gummie with probiotics, or a gummy made from tapioca syrup, a unique, desirable flavor and mouthfeel is obtained and which is also alcohol free. This expands the number of people who can enjoy the benefits of the traditional tea.

30 Claims, No Drawings

(56) References Cited

OTHER PUBLICATIONS

McCarty et al., "Capsaicin may have important potential for promoting vascular and metabolic health"; Open Heart 2015;2:e000262. doi:10.1136/openhrt-2015-000262 (8 Pages).

Montero et al., "Efecto del *Capsicum annum* L (pucunucho, ahi mono) en ulcera gastrica experimental inducida en ratas"; Rev Gastroenterol Peru. Apr.-Jun. 2015; vol. 35(2):141 to 146.

Mousavi et al., "Recent Progress in Chemical Composition, Production, and Pharmaceutical Effects of Kombucha Beverage: A Complementary and Alternative Medicine", Evidence-Based Complementary and Alternative Medicine, vol. 2020, pp. 1 to 14.

Mózsik, "Capsaicin as new orally applicable gastroprotective and therapeutic drug alone or in combination with nonsteroidal anti-inflammatory drugs in healthy human subjects and in patients"; Drug Res. 2014; vol. 68: pp. 209 to 258.

Natural Health Product—Monograph—"Ginger—Zingiber Officinale", Health Canada, Oct. 30, 2018 (5 pages).

Probiotic Kombucha Gummies by "Dear Crissy"; "https://dearcrissy.com/probiotic-kombucha-gummies/", published Mar. 19, 2017 (17 pages).

Qula Kombucha Drink Tabs—Keto-Friendly Water Enhancer (Trial Variety Pack) from Amazon; "https://www.amazon.com/ask/questions/asin/B08BRG3BW8/2/ref=ask_dp_iaw_ql_hza?isAn swered= true#question-Tx4D5KL7VT5C7N" available at least since May 29, 2020.

Vegan Kombucha Probiotic Gummies by "Rejoice Nutrition Wellness, Joanna Brown"; "https://rejoicenutritionwellness.com/vegan-kombucha-probiotic-gummies/", published Sep. 24, 2016 (7 pages).

Denisse, "Mixed Berry Kombucha Gummy Snacks". Le Petit Eats, at least Jan. 27, 2016 (Jan. 27, 2016),, [ online ] [retrieved on Jul. 21, 2022 (Jul. 21, 2022)]. Retrieved from the Internet: https://lepetiteats.com/mixed-berry-kombucha-gummy-snacks/ *whole document* (19 pages).

International Search Report of the International Search Autority for PCT/CA2022/050604 dated Aug. 10, 2022 (4 pages.

Written Opinion of the International Search Authority for PCT/CA2022/050604 dated Aug. 10, 2022 (7 pages).

Coelho Raquel Macedo Dantas et al: "Kombucha: Review", International Journal of Gastronomy and Food Science, vol. 22, Dec. 1, 2020 (Dec. 1, 2020), p. 100272, XP055955265, ISSN: 1878-450X, DOI: 10.1016/j.ijgfs.2020.100272.

Extended European Search Report in European Patent Application 22823709.5 dated Jul. 30, 2024, 8 pages.

KOMBUCHA NATURAL HEALTH PRODUCTS

REFERENCE TO RELATED APPLICATIONS

The instant application is a divisional application of U.S. patent application Ser. No. 17/828,129, filed Mar. 31, 2022, and entitled "KOMBUCHA NATURAL HEALTH PRODUCTS", which in turn, and the instant application, claims benefit of priority to Canadian Patent Application serial number 3,122,201, filed Jun. 14, 2021, and entitled "KOMBUCHA NATURAL HEALTH PRODUCTS", the contents of which is herein fully incorporated by reference.

BACKGROUND ART

Kombucha is a fermented tea. Not only does it have the health benefits of tea it is also rich in beneficial probiotics. Kombucha contains antioxidants such as catechins which have numerous health benefits. The bacteria can improve many aspects of health, including digestion, metabolism and inflammation.

For a review of kombucha tea see for example, Jayabalan et al., Comprehensive Reviews in Food Science and Food Safety Vol. 13, 2014.

For a review of the chemistry and production of kombucha tea beverage see Mousavi et al., Evidence-Based Complementary and Alternative Medicine Volume 2020, Article ID 4397543, https://doi.org/10.1155/2020/4397543.

The health benefits of tea have been well documented (see for example, Aboulwafa et al., Antioxidants 2019, 8, 455).

Kombucha is made by adding specific strains of bacteria, yeast and sugar to black or green tea, then allowing it to ferment. During this process, bacteria and yeast form a mushroom-like film on the surface of the liquid. This is why kombucha is also known as "mushroom tea." This blob is a living symbiotic colony of bacteria and yeast, or a "SCOBY". The fermentation process produces acetic acid and other acidic compounds and trace levels of alcohol. Bacteria also grow in the mixture including several species of lactic-acid bacteria which have probiotic function. Some kombucha teas contain more than trace alcohol, making them unsuitable as a daily health product.

One of the main substances produced during the fermentation of kombucha is acetic acid, like the polyphenols, acetic acid is able to kill many potentially harmful microorganisms. Kombucha has strong antibacterial properties, particularly against infection-causing bacteria and *Candida* yeasts. These antimicrobial effects suppress the growth of undesirable bacteria and yeasts, but they do not affect the beneficial, probiotic bacteria and yeasts involved in kombucha fermentation.

Natural and traditional products, such as kombucha tea, face many challenges concerning their use for their health benefits, especially regarding their standardization, as well as the determination of a specific dosage forms appropriate to the intended use. Kombucha tea, as a fermented, alcohol-containing beverage that relies on a complex combination of living yeast and bacteria for production is especially difficult to administer. Thus the present invention solves these problems and provides a consistent, standardized dosage form and novel combinations of a traditional medicinal drink that is otherwise unsuitable for widespread natural medicine. In addition, the soft, chewable and orally dissolvable and/or disintegrable compositions of the instant invention provide a unique, desirable flavor and mouthfeel and is also alcohol free which expands the number of people who can enjoy the benefits of the traditional tea.

SUMMARY OF THE INVENTION

The following presents a simplified summary of the general inventive concept(s) described herein to provide a basic understanding of some aspects of the disclosure. This summary is not an extensive overview of the disclosure. It is not intended to restrict key or critical elements of embodiments of the disclosure or to delineate their scope beyond that which is explicitly or implicitly described by the following description and claims.

A need exists for kombucha natural health product gummie product that overcome some of the drawbacks of known and product and techniques, or at least, provides a useful alternative thereto. Some aspects of this disclosure provide examples of such a kombucha natural health product gummie product having a prolonged shelf-life The present invention comprises a composition comprising kombucha tea powder plus excipients to form gummies or tablets. Particular embodiments include pre-portioned, soft, chewable and orally dissolvable and/or disintegrable compositions wherein the kombucha tea powder is distributed in a biopolymer-sugar based matrix.

Other compositions according to the invention are an edible dosage form including tapioca starch plus cane sugar in the form of tasty "gummies".

In one aspect, there is provided a gummie composition comprising kombucha tea powder, a biopolymer, and at least 2% by weight of a sugar.

In some embodiments, the kombucha tea powder is distributed in a pre-portioned, soft, chewable and orally dissolvable and/or disintegrable, biopolymer-sugar based matrix.

In some embodiments, the biopolymer is gellan gum, konjac gum, modified starch, tapioca starch, pectin, carrageenan, guar gum, xanthan gum, locust bean gum, agar, gum Arabic, alginate, gelatin, cellulose, or combinations thereof.

In some embodiments, the gummie composition further comprises an edible dosage form including tapioca syrup. In some embodiments the gummie composition comprises about 20% to about 70% tapioca syrup.

In some embodiments the gummie composition comprises, in weight percent, about 1% to about 25% kombucha powder, about 1% to about 35% of the biopolymer, about 2% to about 60% sugar, and up to about 10% additional additives for flavor.

In some embodiments, the gummie composition further comprises coffee extract, green tea extract, herbal extract, or combinations thereof. In some embodiments, the gummie composition further comprises ginger extract, or ginger powder. In some embodiments, the gummie composition further comprises cayenne extract, or cayenne powder.

In some embodiments, the sugar is monosaccharide, fructose, glucose, xylose, disaccharides, sucrose, trehalose, lactose, trisaccharides, polysaccharides, oligosaccharides fructan, inulins, sugar alcohols, sorbitol, xylitol, lactitol, maltitol, or combinations thereof. In some embodiments, the sugar is organic cane sugar.

In some embodiments, the gummie composition further comprises a probiotic.

In some embodiments, the gummie composition is provided as a gummie unit with dimensions of up to about 1 inch in height, up to about 1 inch in width, and up to about 1 inch in length and wherein the soft, chewable and orally dissolvable and/or disintegrable composition has a density of less than about 2.0 g/cm 3.

In some embodiments, the gummie composition is provided as a gummie unit with ranges in size from about 0.1 inch to about 1.0 inch in height, about 0.5 inch to about 1.0 inch in width and about 0.25 to about 1.0 inch in length.

In some embodiments, the gummie composition further comprises (a) at least one vitamin, (b) at least one mineral, (c) at least one nutraceutical, (d) at least one amino acid, (e) at least one energizing agent, (f) at least one soothing agent, (g) at least one sweetener, (h) at least one coloring agent, (i) at least one chemesthesis agent, (j) at least one antioxidant, (k) at least one food-grade emulsifier and/or (l) at least one pH modifier.

In some embodiments, the sugar is a monosaccharide, fructose, glucose, or xylose.

In some embodiments, the biopolymer includes pectin.

In some embodiments, the gummie composition is provided as a pre-portioned, soft, chewable and orally dissolvable and/or disintegrable composition includes about 1 to about 5 weight % of flavor beads comprising a solid, liquid or gel center and a hard outer coating, the flavor beads having a diameter of about 0.5 mm to about 4 mm. In some embodiments, the pre-portioned, soft, chewable and orally dissolvable and/or disintegrable composition includes a hard outer coating comprising a polymeric coating. In some embodiments, the hard outer coating has a rough surface. In some embodiments, the flavor beads are contained in a center of the pre-portioned, soft, chewable and orally dissolvable and/or disintegrable composition and/or on the exterior of the soft, chewable and orally dissolvable and/or disintegrable composition.

In another aspect, there is provided a soft, chewable and orally dissolvable and/or disintegrable composition comprising bacterial and yeast treated tea powder, a biopolymer, and at least 2% by weight of a sugar.

In some embodiments, the biopolymer is derived from non-animal sources.

In some embodiments, soft, chewable and orally dissolvable and/or disintegrable composition comprises about 50% tapioca syrup, 21% by weight sugar, 17% by weight water, 2% by weight flavor, 2% by weight pectin, 2% by weight buffering agent or base, 5% by weight kombucha powder, and color.

In some embodiments, the soft, chewable and orally dissolvable and/or disintegrable composition, comprises syrup, cane sugar, water, flavor, pectin, citric acid, kombucha powder, sodium citrate, and a coloring agent.

In some embodiments, the soft, chewable and orally dissolvable and/or disintegrable composition, further comprises an added probiotic.

In yet another aspect, there is provided a method for producing a soft, chewable and orally dissolvable and/or disintegrable composition comprising:
  providing a bacterial and yeast treated tea powder, a biopolymer, and at least 2% by weight of a sugar;
  mixing the bacterial and yeast treated tea powder, the biopolymer, and the at least 2% by weight of the sugar with a suitable amount of water so as to dissolve at least the sugar and the biopolymer in the water flowable mixture; and
  allowing the flowable mixture to gel so as to form the soft, chewable and orally dissolvable and/or disintegrable composition.

In some embodiments of the method, the bacterial and yeast treated tea powder is a kombucha powder.

In some embodiments of the method, the soft, chewable and orally dissolvable and/or disintegrable composition, comprises wherein the bacterial and yeast treated tea powder is provided having a mesh size of less than a 50 mesh. In some embodiments, the soft, chewable and orally dissolvable and/or disintegrable composition, comprises the bacterial and yeast treated tea powder is provided having a mesh size of less than a 200 mesh. In some embodiments, the soft, chewable and orally dissolvable and/or disintegrable composition, comprises the bacterial and yeast treated tea powder is provided having a mesh size of less than a 400 mesh.

In some embodiments of the method, the soft, chewable and orally dissolvable and/or disintegrable composition, comprises bacterial and yeast treated tea powder is distributed in a pre-portioned, soft, chewable and orally dissolvable and/or disintegrable, biopolymer-sugar based matrix.

In some embodiments of the method, the soft, chewable and orally dissolvable and/or disintegrable composition, comprises the biopolymer is gellan gum, konjac gum, modified starch, tapioca starch, pectin, carrageenan, guar gum, xanthan gum, locust bean gum, agar, gum Arabic, alginate, gelatin, cellulose, or combinations thereof.

In some embodiments, the method further comprises adding an edible dosage form including tapioca syrup to the flowable mixture. In some embodiments of the method, tapioca syrup comprises about 20% to about 70% of the flowable mixture.

In some embodiments of the method, in weight percent, there is provided about 1% to about 25% kombucha powder, about 1% to about 35% of the biopolymer, about 2% to about 60% sugar, and up to about 10% additional additives for flavor is provided to form the flowable mixture.

In some embodiments, the method further comprises adding coffee extract, green tea extract, herbal extract, or combinations thereof, to the flowable mixture.

In some embodiments, the method further comprises adding ginger extract, or ginger powder, to the flowable mixture.

In some embodiments, the method further comprises adding cayenne extract, or cayenne powder, to the flowable mixture.

In some embodiments of the method, the sugar is monosaccharide, fructose, glucose, xylose, disaccharides, sucrose, trehalose, lactose, trisaccharides, polysaccharides, oligosaccharides, fructan, inulins, sugar alcohols, sorbitol, xylitol, lactitol, maltitol, or combinations thereof. In some embodiments of the method, the sugar is organic cane sugar.

In some embodiments, the method further comprises adding a probiotic to the flowable mixture.

In some embodiments, the method further comprises adding the flowable mixture to a vessel for gelling so as to form the soft, chewable and orally dissolvable and/or disintegrable composition to shape having up to about 1 inch in height, up to about 1 inch in width, and up to about 1 inch in length.

In some embodiments, the method further comprises adding the flowable mixture to a vessel for gelling so as to form the soft, chewable and orally dissolvable and/or disintegrable composition ranges in size from about 0.1 inch to about 0.5 inch in height, about 0.5 inch to about 1.0 inch in width and about 0.25 to about 0.5 inch in length.

In some embodiments of the method, the soft, chewable and orally dissolvable and/or disintegrable composition has a density of less than about 2.0 g/cm 3.

In some embodiments, the method further comprises adding one or more of: (a) at least one vitamin, (b) at least one mineral, (c) at least one nutraceutical, (d) at least one amino acid, (e) at least one energizing agent, (f) at least one soothing agent, (g) at least one sweetener, (h) at least one coloring agent, (i) at least one chemesthesis agent, (j) at least one antioxidant, (k) at least one food-grade emulsifier and/or (l) at least one pH modifier, to the flowable mixture.

In some embodiments of the method, the biopolymer includes pectin.

In some embodiments of the method, the method further comprises adding about 1 to about 5 weight % of flavor beads comprising a solid, liquid or gel center and a hard outer coating, the beads having a diameter of about 0.5 mm to about 4 mm, to the flowable mixture.

In some embodiments, the method further comprises providing a hard outer coating comprising a polymeric coating to the soft, chewable and orally dissolvable and/or disintegrable composition. In some embodiments of the method, the hard outer coating has a rough surface.

In some embodiments of the method, the biopolymer is derived from non-animal sources.

In some embodiments of the method, the biopolymer is pectin.

In some embodiments, the method further comprises adding a probiotic to the flowable mixture.

Other aspects, features and/or advantages will become more apparent upon reading of the following non-restrictive description of specific embodiments of the disclosed kombucha natural health product given by way of example only.

DETAILED DESCRIPTION

The present invention discloses novel dosage forms and combinations of kombucha tea powder. The dosage forms include soft, chewable and orally dissolvable and/or disintegrable compositions (preferably "gummies") or monolithic matrix tablets.

The gummies and tablets according to the present invention contain various active nutrients, which can help with detoxification, gastrointestinal health, antioxidant effects and other health benefits. In addition, certain embodiments of the kombucha soft, chewable and orally dissolvable and/or disintegrable compositions of the present invention are formulated to have a unique taste, retaining the essential kombucha tea flavor.

Certain embodiments of the present invention include at least one additional incipients and excipients—active and inactive additives. Suitable additives include, without limitation, vitamins, minerals, nutraceuticals, energizing agents, soothing agents, amino acids, chemesthesis agents, antioxidants, flavorants, colorants, food grade emulsifiers, pH modifiers, and/or combinations thereof. The additives can be included in the compositions in an amount of up to about 20 wt % (e.g., about 1 wt % to about 5 wt % or about 5 wt % to about 10 wt %).

Suitable soothing agents include, without limitation, chamomile, lavender, jasmine, and the like.

Suitable vitamins according to certain embodiments of the invention include, without limitation, vitamin A (retinol), vitamin D (cholecalciferol), vitamin E group, vitamin K group (phylloquinones and menaquinones), thiamine (vitamin $B_1$), riboflavin (vitamin $B_2$), niacin, niacinamide, pyridoxine (vitamin $B_6$ group), folic acid, choline, inositol, vitamin $B_{12}$ (cobalamins), PABA (para-aminobezoic acid), biotin, vitamin C (ascorbic acid), and mixtures thereof.

The amount of vitamins incorporated into soft, chewable and orally dissolvable and/or disintegrable compositions can be varied according to the type of vitamin and the intended user of the soft, chewable and orally dissolvable and/or disintegrable product.

The chemesthesis ingredients according to certain embodiments can provide, without limitation, hot, spicy, or cooling flavors. Suitable chemesthesis agents include, without limitation, capsaicin, tannins, mustard oil, wintergreen oil, cinnamon oil, allicin, quinine, citric acid, and salt.

As used herein, the term "nutraceuticals" refers to any ingredient in foods that has a beneficial effect on human health. Nutraceuticals include particular compounds/compositions isolated from food sources. For example, nutraceuticals include various phytonutrients derived from plants.

Suitable minerals include, without limitation, calcium, magnesium, phosphorus, iron, zinc, iodine, selenium, potassium, copper, manganese, molybdenum, chromium, and mixtures thereof. The amount of minerals incorporated into the soft, chewable and orally dissolvable and/or disintegrable composition can be varied according to the type of vitamin and the intended user. For example, the amount of minerals may be formulated to include an amount equal to the recommendations of the United States Department of Agriculture Recommended Daily Allowances. In some embodiments such recommendations may be exceeded in order to achieve a specific health benefit.

Suitable amino acids according to the invention include, without limitation, the eight essential amino acids that cannot be biosynthetically produced in humans, including valine, leucine, isoleucine, lysine, threonine, tryptophan, methionine, and phenylalanine. Examples of suitable amino acids include the non-essential amino acids including alanine, arginine, asparagine, aspartic acid, cysteine, glutamic acid, glutamine, glycine, histidine, proline, serine, and tyrosine.

In another embodiment, the composition can include various active agents having antioxidant properties that can delay the ageing process, as food-grade ingredients. For example, the active ingredients that can be extracted from *Ginkgo biloba* include flavonoid glycosides ("ginkgoflavonoids"), such as (iso)quercitin, kaempferol, kaempferol-3-rhamnosides, isorhamnetin, luteolin, luteolin glycosides, sitosterol glycosides, and hexacyclic terpene lactones, referred to as "ginkgolides" or "bilobalides." The active ingredients that can be extracted from *Vaccinium myrtillus*, such as blueberry, include at least 15 different anthocyanosides, such as delphinidin, anthocyanosides, myrtin, epimyrtin, phenolic acids, glycosides, quercitrin, isoquercitrin, and hyperoside. The active ingredients that can be extracted from Vinis vitifera, such as grapes, include polyphenols, catechols, quercitrins, and resveratrols. The active ingredients that can be extracted from *Olea* europensis, such as the leaves of olive trees, include oleuropein. Many active ingredients identified from these and other plant sources associated with the neutralization of free radicals and useful for delaying the ageing process are contemplated. Other antioxidants known in the art are also contemplated.

In a specific preferred embodiment of the compositions of the present invention, the composition further comprises a ginger extract.

As used herein, and unless the context in which they occur implicitly or explicitly suggest another meaning for these terms, the terms "ginger" refers to the root and rhizome of the plants, parts thereof or extracts thereof. Ginger (*Zingiber officinale*) is also called "warming herb".

Ginger is generally recognized as safe for human consumption by the German Commission E, (Blumenthal M, 1998) and Health Canada. Health Canada has recognized the use of ginger rhizomes as an expectorant and cough suppressant to help relieve bronchitis as well as coughs and colds. Canadian Natural Health Product Monograph—Ginger—*Zingiber officinale* (Oct. 30, 2018). Rhizomes are a horizontal underground plant stem capable of producing the shoot and root systems of a new plant. Rhizomes are used to store starches and proteins and enable plants to survive an annual unfavorable season underground.

Ginger has a wide area of usage. Ginger may be preventive against cancer based on its antiviral activity against the Epstein-barr virus. 6-gingerol and 6-paradol, among the active substances of ginger, may be effective in stopping promyelocytic leucaemia by disturbing the DNA synthesis. It supports the cardiovascular system by making the platelets less adherent, this in turn causes a decrease in the problems of circulation system. It is appetizing and can also be used against constipation. In addition to these, it has a warming and sedative effect in cough, flu, cold and other respiratory system diseases.

In another embodiment, the combination comprises concentrated ginger powder.

In another embodiment, the ginger extract is a crude ginger extract. In another embodiment, the ginger extract is a crude 100% water ginger extract. In another embodiment, the ginger extract is a $CO_2$ ginger extract. In another embodiment, the ginger extract is a crude ginger extract. In another embodiment, the ginger extract is a crude 100% water ginger extract. In another embodiment, the ginger extract is an alcoholic ginger extract. In another embodiment, the alcoholic ginger extract is a hydroalcoholic ginger extract. In another embodiment, the alcohol used for production of the hydroalcoholic extract comprises a primary alcohol. In another embodiment, the primary alcohol is methanol, ethanol, 1-propanol, 1-butanol or any combination thereof. In another embodiment, the primary alcohol used is ethanol. In another embodiment, the alcohol used for production of the hydroalcoholic extract comprises a secondary alcohol. In another embodiment, a mixture of at least two different alcohols is used. In another embodiment, the alcoholic extract is prepared using a solution comprising between about 20% and about 85% of alcohol. In another embodiment, the extract is prepared using a solution comprising 60% of alcohol. In another embodiment, the extract is prepared using a solution comprising about 30% of alcohol. In another embodiment the ginger extract is an 8:1 concentrated extract.

In another embodiment the ginger is a concentrate. In another embodiment the ginger concentrate is an 8:1 concentrate.

The active ingredients of *Trifolium pratense*, such as purple clovers (i.e., common purple trefoils), include isoflavones or isoflavone glucosides, daidzein, genestein, formononentin, biochanin A, ononin, and sissostrin. The health-promoting properties of compounds derived from *Panax*, a genus that includes *Ginseng*, are well-established. These and other botanicals, kombucha extracts, and bioactive compounds having health promoting effects are contemplated.

The kombucha powder of the instant invention comprises polyphenols, such as epicatechol, epigallocatechol, epigallocatechol gallate, epigallocatechol gallate, theaflavin, theaflavin monogallate A or B, and theaflavin digallate.

Embodiments of the instant invention include combinations of kombucha powder plus herbals such as *garcinia cambogia* and extracts thereof standardized for hydroxycitric acid.

In certain embodiments energizing ingredients may include, without limitation, caffeine, taurine, and guaran. Additionally, caffeine and/or other thermogenic ingredients can be added to increase the metabolic and weight loss properties.

In other preferred embodiments, cayenne pepper (*Capsicum annuum*) powder or extracts are included as a thermogenic ingredient.

Cayenne raises metabolic rates, increases thermogenesis, decreases appetite, and causes weight loss. Janssens et al., Appetite. 2014 June; 77:44-9. Chaiyata P, Puttadechakum S, Komindr S. Effect of chili pepper (*Capsicum frutescens*) ingestion on plasma glucose response and metabolic rate in Thai women. J Med Assoc Thai. 2003 September; 86(9): 854-60. PMID: 14649970. Galgani J E, Ravussin E. Effect of dihydrocapsiate on resting metabolic rate in humans. Am J Clin Nutr. 2010 November; 92(5):1089-93. doi: 10.3945/ajcn.2010.30036. Epub 2010 Sep. 8. PMID: 20826626; PMCID: PMC2954444. Ludy M J, Mattes R D. The effects of hedonically acceptable red pepper doses on thermogenesis and appetite. Physiol Behav. 2011 Mar. 1; 102(3-4): 251-8. doi: 10.1016/j.physbeh.2010.11.018. Epub 2010 Nov. 18. PMID: 21093467; PMCID: PMC3022968.

Cayenne and its constituents also reduce ulcers (Delgado Montero R, Flores Cortez D, Villalobos Pacheco E. Efecto del *Capsicum* annum L (pucunucho, ají mono) en úlcera gástrica experimental inducida en ratas [Effect of *Capsicum* annum L (pucunucho, ají mono) in gastric ulcer experimentally induced in rats]. Rev Gastroenterol Peru. 2015 April-June; 35(2):141-6. PMID: 26228980); has anti-inflammatory and gastroprotective properties (Mózsik G. (2014) Capsaicin as New Orally Applicable Gastroprotective and Therapeutic Drug Alone or in Combination with Nonsteroidal Anti-Inflammatory Drugs in Healthy Human Subjects and in Patients. In: Abdel-Salam O. (eds) Capsaicin as a Therapeutic Molecule. Progress in Drug Research, vol 68. Springer, Basel. https://doi.org/10.1007/978-3-0348-0828-6_9); has positive vascular effects (McCarty M F, DiNicolantonio J J, O'Keefe J H Capsaicin may have important potential for promoting vascular and metabolic health Open Heart 2015; 2:e000262. doi: 10.1136/openhrt-2015-000262).

Cayenne has also been proven to have pain relieving properties. Deal et al., Treatment of arthritis with topical capsaicin: a double-blind trial. Clinical Therapeutics 1991; 13(3):383-395.

Natural kombucha tea contains probiotics derived from the fermentation process and the SCOBY. The process of developing a dried dosage form of the tea may impact the quality and quantity of the probiotics and so in certain preferred embodiments of the invention probiotics are included to achieve all of the health benefits naturally derived from consuming kombucha tea.

Certain embodiments of the present invention comprise soft, chewable and orally dissolvable and/or disintegrable compositions further comprise a biopolymer-sugar based matrix and kombucha powder. Preferably, the biopolymer-sugar based matrix includes at least one biopolymer, which acts as a binder, and at least one sugar, which acts as a co-binder. Preferably, the soft, chewable and orally dissolvable and/or disintegrable composition can be chewed by a user until substantially all of the ingredients contained therein substantially dissolve and disintegrate in the user's mouth.

A soft, chewable and orally dissolvable and/or disintegrable composition comprising a biopolymer-sugar based matrix and kombucha tea powder in an amount sufficient to form at least about 30 wt % to about 75 wt % of the soft, chewable and orally dissolvable composition is provided. The biopolymer-sugar based matrix comprises at least one biopolymer in an amount of about 1 to about 35 wt % of the soft, chewable and orally dissolvable composition and at least one sugar in an amount of about 2 wt % to about 60 wt % of the soft, chewable and orally dissolvable and/or disintegrable composition. The soft, chewable and orally dissolvable and/or disintegrable composition is chewable in a user's mouth before dissolving and disintegrating in an oral cavity of a user. Also, the at least one sugar is included in an amount sufficient to substantially inhibit cross-linking between the at least one kombucha powder and the at least one biopolymer.

In an embodiment, the soft, chewable and orally dissolvable and/or disintegrable composition can also include flavor beads to add additional texture and flavor to the soft, chewable and orally dissolvable and/or disintegrable composition. The flavor beads can include a polymer coating. The polymer coating can be abrasive. Preferably, the beads have diameters of about 0.5 mm to about 4.0 mm.

In certain embodiments, the kombucha powder is provided as a monolithic matrix tablet comprising organic gum acacia, coating (organic maltodextrin, organic sunflower lecithin, organic palm olein, organic guar gum), organic rice hull concentrate, organic rice bran extract, organic rice hulls, organic gum arabic, organic sunflower oil.

In a preferred embodiment, the soft, chewable and orally dissolvable and/or disintegrable composition is free of animal products, such as gelatin. Preferably, animal products, such as gelatin, are not included in the matrix so as to prevent hardening of the matrix prior to use. In addition, by not including gelatin and/or other animal products, the soft, chewable and orally dissolvable and/or disintegrable composition is acceptable for use by vegans, users with allergies, and/or users with cultural and religious beliefs, which discourage consumption of animal products. In addition, the lack of animal products in the soft, chewable and orally dissolvable and/or disintegrable composition prevents the transmission of possible diseases associated with animal tissues, such as bovine spongiform encephalopathy. In a preferred embodiment, the soft, chewable and orally dissolvable and/or disintegrable composition can also be organic.

In certain embodiments a softener and/or plasticizer, such as glycerin, can optionally be used to add additional softness to the biopolymer-sugar based matrix.

As used herein, the terms "soft," "soften" and "softness" describes the soft, chewable and orally dissolvable and/or disintegrable compositions containing kombucha powder in a relatively malleable state. Preferably, the composition is firm, but not hard.

Preferably, the soft, chewable and orally dissolvable and/or disintegrable composition includes at least one biopolymer in an amount of about 1 wt % to about 35 wt %, more preferably about 2 wt % to about 20 wt % (e.g., about 2 wt % to about 5 wt %, about 5 wt % to about 10 wt %, about 10 wt % to about 15 wt % or about 15 wt % to about 20 wt %).

Suitable biopolymers include, without limitation, agar, alginate, carrageenans, such as iota carrageenan and kappa carrageenan, cellulose, gellan gum, gelatin, guar gum, gum Arabic, konjac gum, locust bean gum, modified starch, pectin, xanthan gum, and/or combinations thereof.

In the preferred embodiment, the soft, chewable and orally dissolvable and/or disintegrable composition also includes a sugar. Preferably, the sugar provides both softening and sweetening of the soft, chewable and orally dissolvable and/or disintegrable composition. Also preferably, the sugar is included in an amount of about 2 wt % to about 60 wt %, more preferably about 5 wt % to about 30 wt % (e.g., about 5 wt % to about 25 wt %, about 10 wt % to about 20 wt %, about 15 wt % to about 20 wt %, about 20 wt % to about 25 wt % or about 15 wt % to about 30 wt %).

In a preferred embodiment, the gummy does not harden even with prolonged exposure to air. Not wishing to be bound by theory, it is believed that the sugar forms hydrogen bonds with the biopolymer and blocks binding sites thereof to prevent cross-linking between the biopolymer and the kombucha powder. By preventing cross-linking between the biopolymer and the kombucha powder, the soft, chewable and orally dissolvable and/or disintegrable composition maintains a soft consistency as compared to oral compositions that contain cross-linked polymers. Thus, if less than 2 wt % sugar is used, not all of the active sites of the biopolymer will be blocked, thereby allowing some cross-linking to occur, which results in the formation of a harder matrix. Alternatively, if sugar is used in larger amounts the active sites of the biopolymer will be completely blocked to form a soft composition, and any excess sugar will act to sweeten the soft, chewable and orally dissolvable composition.

Preferred sugars are organic cane sugars, however, other suitable sugars may be used. Additional preferred sugars are small molecule saccharides, such as honey and/or high fructose corn syrup. However, other suitable sugars include, without limitation, monosaccharides (e.g., fructose, glucose, xylose, etc.), disaccharides (e.g., sucrose, trehalose, lactose, etc.), trisaccharides, polysaccharides, oligosaccharides (e.g., fructan and inulins), sugar alcohols (e.g., sorbitol, xylitol, lactitol, maltitol, etc.), and mixtures of sugars (e.g., combinations of honey, corn syrups, light corn syrups and/or high fructose corn syrups, etc.). Additionally, sweeteners, such as sucralose and *stevia* or derivatives thereof can be used.

Especially preferred embodiments of the soft, chewable and orally dissolvable and/or disintegrable compositions of the present invention include a significant amount of tapioca powder or syrup. In certain preferred embodiments the chewable compositions include between 40 and 60 wt % tapioca syrup. The combination of tapioca and kombucha provides a unique taste and mouth feel.

Certain preferred embodiments of the present invention will include organic tapioca powder. Tapioca is a starch extracted from the storage roots of the cassava plant (*Manihot esculenta*, also known as manioc), a species native to the north and central-west regions of Brazil, but whose use is now spread throughout South America. The plant was brought by the Portuguese to much of the West Indies, Africa and Asia. It is a perennial shrub adapted to the hot conditions of tropical lowlands. Cassava copes better with poor soils than many other food plants.

In the north and northeast of Brazil, traditional community-based production of tapioca is a by-composition of manioc flour production from cassava roots. The liquid by-product of flour production is collected and the (microscopic) starch grains in it are allowed to settle to the bottom of the container. The supernatant liquid is then poured off, leaving behind a wet starch sediment that needs to be dried and results in the fine-grained tapioca starch powder similar in appearance to corn starch.

Commercially, the tapioca starch is processed into several forms: hot soluble powder, meal, pre-cooked fine/coarse flakes, rectangular sticks, and spherical "pearls" as well as syrup.

Suitable flavorants include any flavorants commonly used in foods, confections and oral products. Exemplary flavorants include, but are not limited to, berry flavors such as pomegranate, acai, raspberry, blueberry, strawberry, boysenberry, and/or cranberry. Other suitable flavorants include, without limitation, any natural or synthetic flavor or aroma, such as menthol, peppermint, spearmint, wintergreen, bourbon, scotch, whiskey, cognac, *hydrangea*, lavender, chocolate, licorice, citrus and other fruit flavors, such as apple, peach, pear, cherry, plum, orange, lime, grape, and grapefruit, gamma octalactone, vanillin, ethyl vanillin, breath freshener flavors, butter, rum, coconut, almond, pecan, walnut, hazelnut, French vanilla, macadamia, sugar cane, maple, cassis, caramel, banana, malt, espresso, kahlua, white chocolate, spice flavors such as cinnamon, clove, cilantro, basil, oregano, garlic, mustard, nutmeg, rosemary, thyme, tarragon, dill, sage, anise, and fennel, methyl salicylate, linalool, jasmine, coffee, olive oil, sesame oil, sunflower oil, bergamot oil, geranium oil, lemon oil, ginger oil, balsamic vinegar, rice wine vinegar, and red wine vinegar.

The flavorants can be incorporated in the matrix or applied to the soft, chewable and orally dissolvable and/or disintegrable composition by spraying, coating, immersing, embossing, and/or dispersing them into or onto the soft, chewable and orally dissolvable composition itself. In an embodiment, the flavorants are added in the form of spray dried flavorants, essential oils, and/or solutions. In other embodiments, the flavorants can be added to the biopolymer solution during formation of the soft, chewable and orally dissolvable product.

Suitable pH modifiers include, without limitation, $Na_2CO_3$, $NaHCO_3$, $K._3PO_4$, $K_3HPO_4$, NaOH, HCl, citric acid and combinations thereof. pH modifiers can be added to adjust the flavor of the soft, chewable and orally dissolvable and/or disintegrable composition. Since some polymers tend to be acidic by nature, a pH modifier can be included to neutralize the taste of the soft, chewable and orally dissolvable composition. Preferably, the soft, chewable and orally dissolvable and/or disintegrable composition has a pH of about 3 to about 8, more preferably about 3 to about 5.

In an embodiment, the soft, chewable and orally dissolvable and/or disintegrable composition can include a food-grade emulsifier. Preferably, the food-grade emulsifier is added when oil based flavorants, such as wintergreen oil, are included in the soft, chewable and orally dissolvable composition to stabilize the flavorant within the hydrocolloid based matrix. Typically, food-grade emulsifiers are not necessary for use with water based flavorants. However, food-grade emulsifiers can be used with water based flavorants if desired. Suitable food-grade emulsifiers include, without limitation, phospholipids, such as lecithins, fatty acid mono- and di-glycerides, phosphated monoglycerides, glycerol esters, such as glycerol monooleate, glycerol monotallate, polyglycerol oleate and/or polyglycerol decaoleate, sorbitan esters, such as sorbitan monolaurate, sorbitan monostearate, sorbitan monooleate and/or sorbitan trioleate, and/or polysorbates (e.g., Polysorbate 20 and/or Polysorbate 80).

In the preferred embodiment, the soft, chewable and orally dissolvable and/or disintegrable composition includes at least one kombucha powder in an amount of up to about 75 wt % by weight based on the weight of the soft, chewable and orally dissolvable product, more preferably about 30 wt % to about 75 wt % (e.g., about 45 wt % to about 55 wt %, about 55 wt % to about 65 wt % or about 65 wt % to about 75 wt %). In a preferred embodiment, the kombucha material disintegrates in the user's mouth.

As used herein, the term "kombucha powder" describes dust, fines, colloidal dispersions, granules, dried kombucha tea and the like having dimensions of less than about 50 mesh, more preferably less than about 200 mesh and most preferably less than about 400 mesh. In an embodiment, the soft, chewable and orally dissolvable composition can also include kombucha powder as described above. The smaller the kombucha powder, the less gritty the soft, chewable and orally dissolvable and/or disintegrable composition may feel in a user's mouth. In addition, the use of smaller kombucha powders results in faster disintegration of the powders.

In an embodiment, if the soft, chewable and orally dissolvable and/or disintegrable composition includes kombucha powder, the orally dissolvable composition can also include at least one non-kombucha flavorant.

Preferably, about 0.01 mg to about 100 mg of a flavorant is added to the soft, chewable and orally dissolvable and/or disintegrable composition 10. The amount of flavorant added can depend on the type and/or potency of the flavorant being added, but is preferably added in an amount of up to about 15 wt %, more preferably up to about 10 wt %. In an embodiment, the soft, chewable and orally dissolvable and/or disintegrable composition can include multiple flavorants.

For example, a preferred soft, chewable and orally dissolvable and/or disintegrable composition can comprise about 50 wt % kombucha powder, about 20% biopolymer binder, about 20 wt % sugar co-binder, about 3 wt % flavorant and sweeteners and about 7 wt % other additives.

Preferably, the shelf-life of the soft, chewable and orally dissolvable and/or disintegrable composition is preferably at least about 6 months and most preferably at least about 36 months. Despite the low moisture content, the soft, chewable and orally dissolvable and/or disintegrable composition could theoretically still suffer from chemical oxidation and/or loss of flavor. Thus, the shelf-life may be increased and/or decreased based on the ingredients of the soft, chewable and orally dissolvable and/or disintegrable composition and changes therein over time.

Since the soft, chewable and orally dissolvable and/or disintegrable composition includes an amount of water, some hardening may take place over time due to drying. However, because the water content is low, the hardening resulting from drying is substantially unnoticeable to consumers. In embodiments, additional water can be added to increase plasticity of the soft, chewable and orally dissolvable and/or disintegrable composition if desired.

In a preferred embodiment, the soft, chewable and orally dissolvable and/or disintegrable composition is cut into shapes and/or molded before and/or after gelation to form suitably sized, pre-portioned pieces of soft, chewable and orally dissolvable and/or disintegrable composition. In an embodiment, the composition can be extruded.

The following examples of methods of preparing kombucha and incorporating the kombucha in soft, chewable and orally dissolvable and/or disintegrable composition are exemplary and are not meant to limit any aspects of the embodiments disclosed herein.

EXAMPLE 1

About 4.5 to about 5 g gummies are provided. A biopolymer binder and sugar co-binder are added to form a mixture. The mixture can be gelled to form a soft, chewable and orally dissolvable and/or disintegrable composition including SCOBY treated kombucha powder.

TABLE 1

Gummie composition

| Active | Raw per Gummy Gummy | Units | % Composition | Function |
|---|---|---|---|---|
| Organic tapioca syrup | 2268.9 | mg | 50.42 | Base Ingredient/ biopolymer |
| Organic Cane | 941.85 | mg | 20.93 | Base Ingredient/ co-binder |
| Water | 783 | mg | 17.40 | Base Ingredient |
| Fruit Punch Flavor | 92.7 | mg | 2.06 | Flavor |
| Pectin | 87.3 | mg | 1.94 | Gelling Agent/ Biopolymer |
| Citric Acid | 75.15 | mg | 1.67 | Buffering Acid |
| Kombucha | 225 | mg | 5.00 | Active Ingredient |
| Sodium Citrate | 16.65 | mg | 0.37 | Buffering Base |
| ExBerry | 9.45 | mg | 0.21 | Color |

TABLE 2

Physical & Chemical Properties of kombucha powder

| | |
|---|---|
| Appearance | Brown powder |
| Odor & Flavor | Black tea scent |
| Moisture | Max. 5% |
| pH value (10% sol'n) | 3-5 |
| Acidity as citric acid <Organic Acid> | Min. 1% |
| Polyphenol | Min. 6000 ppm |
| Flavonoids | Min. 6000 ppm |
| Caffeine | 0.1-0.2% |

While the foregoing describes in detail an soft, chewable and orally dissolvable and/or disintegrable composition that is chewable, dissolvable and disintegrable in the oral cavity with reference to specific embodiments thereof, it will be apparent to one skilled in the art that various changes and modifications equivalents to the soft, chewable and orally dissolvable and/or disintegrable composition and process steps may be employed, which do not materially depart from the spirit and scope of the invention. Accordingly, all such changes, modifications, and equivalents that fall within the spirit and scope of the invention as defined by the appended claims are intended to be encompassed thereby.

We claim:

1. A method for producing a soft, chewable and orally dissolvable and/or disintegrable composition comprising:
   providing tapioca, a bacterial and yeast treated tea powder, a biopolymer, and at least 2% by weight of a sugar;
   mixing the tapioca, bacterial and yeast treated tea powder, the biopolymer, and the at least 2% by weight of the sugar with a suitable amount of water so as to dissolve at least the sugar and the biopolymer in the water to provide a flowable mixture; and
   allowing the flowable mixture to gel so as to form the soft, chewable and orally dissolvable and/or disintegrable composition.
2. The method of claim 1, wherein the bacterial and yeast treated tea powder is a kombucha powder.
3. The method of claim 1, wherein the bacterial and yeast treated tea powder is provided having a mesh size of less than a 50 mesh.
4. The method of claim 1, wherein the bacterial and yeast treated tea powder is provided having a mesh size of less than a 200 mesh.
5. The method of claim 1, wherein the bacterial and yeast treated tea powder is provided having a mesh size of less than a 400 mesh.
6. The method of claim 1, wherein the biopolymer is gellan gum, konjac gum, modified starch, pectin, carrageenan, guar gum, xanthan gum, locust bean gum, agar, gum Arabic, alginate, gelatin, cellulose, or combinations thereof.
7. The method of claim 1, wherein the tapioca includes tapioca syrup.
8. The method of claim 7, wherein the tapioca syrup comprises about 20% to about 70% by weight of the flowable mixture.
9. The method of claim 1, wherein, in weight percent of the flowable mixture, about 1% to about 25% kombucha powder, about 1% to about 35% biopolymer, about 2% to about 60% sugar, and up to about 10% additional additives for flavor, is provided to form the flowable mixture.
10. The method of claim 1, further comprising adding coffee extract, green tea extract, herbal extract, or combinations thereof, to the flowable mixture.
11. The method of claim 1, further comprising adding ginger extract, or ginger powder, to the flowable mixture.
12. The method of claim 1, further comprising adding cayenne extract, or cayenne powder, to the flowable mixture.
13. The method of claim 1, wherein the sugar is a monosaccharide, a disaccharide, a trisaccharide, a polysaccharide, an oligosaccharide, or combinations thereof.
14. The method of claim 1, wherein the sugar is fructose, glucose, xylose, sucrose, trehalose, fructan, inulins, sugar alcohols, sorbitol, xylitol, lactitol, maltitol, or combinations thereof.
15. The method of claim 1, wherein the sugar is organic cane sugar.
16. The method of claim 1, further comprising adding a probiotic to the flowable mixture.
17. The method of claim 1, further comprising transferring the flowable mixture to a vessel for gelling so as to form the soft, chewable and orally dissolvable and/or disintegrable composition into a shape having up to about 1 inch in height, up to about 1 inch in width, and up to about 1 inch in length.
18. The method of claim 1, further comprising transferring the flowable mixture to a vessel for gelling so as to form the soft, chewable and orally dissolvable and/or disintegrable composition ranges into a size from about 0.1 inch to about 0.5 inch in height, about 0.5 inch to about 1.0 inch in width and about 0.25 to about 0.5 inch in length.
19. The method of claim 1, further comprising adding one or more of: (a) at least one vitamin, (b) at least one mineral, (c) at least one nutraceutical, (d) at least one amino acid, (e) at least one energizing agent, (f) at least one soothing agent, (g) at least one sweetener, (h) at least one coloring agent, (i) at least one chemesthesis agent, (j) at least one antioxidant, (k) at least one food-grade emulsifier and/or (l) at least one pH modifier, to the flowable mixture.
20. The method of claim 1, wherein the biopolymer includes pectin.
21. The method of claim 1, further comprising adding to the flowable mixture about 1 to about 5 weight % of flavor beads comprising a solid, liquid, or gel center and a hard outer coating, the flavor beads having a diameter of about 0.5 mm to about 4 mm.
22. The method of claim 1, further comprising providing a hard outer coating comprising a polymeric coating to the soft, chewable and orally dissolvable and/or disintegrable composition.

23. The method of claim 1, wherein the biopolymer is derived from non-animal sources.

24. The method of claim 1, further comprising adding a probiotic to the flowable mixture.

25. The method of claim 1, wherein the tapioca includes tapioca powder.

26. The method of claim 25, wherein the tapioca powder comprises about 20% to about 70% by weight of the flowable mixture.

27. The method of claim 1, wherein the tapioca is tapioca syrup and the composition comprises about 50% tapioca syrup, 21% by weight sugar, 17% by weight water, 2% by weight flavor, 2% by weight pectin, 2% by weight buffering agent or base, 5% by weight kombucha powder, and color.

28. The method of claim 1, wherein the tapioca is tapioca powder and the composition comprises about 50% tapioca powder, 21% by weight sugar, 17% by weight water, 2% by weight flavor, 2% by weight pectin, 2% by weight buffering agent or base, 5% by weight kombucha powder, and color.

29. The method of claim 1, wherein the composition comprises tapioca syrup, cane sugar, water, flavor, pectin, citric acid, kombucha powder, sodium citrate, and a coloring agent.

30. The method of claim 1, wherein the composition comprises tapioca powder, cane sugar, water, flavor, pectin, citric acid, kombucha powder, sodium citrate, and a coloring agent.

\* \* \* \* \*